US008846333B2

(12) United States Patent
Karlsson

(10) Patent No.: US 8,846,333 B2
(45) Date of Patent: Sep. 30, 2014

(54) METHOD AND DEVICE FOR VISUAL DETECTION OF HEMOLYSIS

(75) Inventor: Mathias Karlsson, Karlstad (SE)

(73) Assignee: Hemcheck Sweden AB, Karlstad (SE)

( * ) Notice: Subject to any disclaimer, the term of this patent is extended or adjusted under 35 U.S.C. 154(b) by 0 days.

(21) Appl. No.: 13/643,115

(22) PCT Filed: Jun. 10, 2011

(86) PCT No.: PCT/SE2011/050718
§ 371 (c)(1),
(2), (4) Date: Oct. 24, 2012

(87) PCT Pub. No.: WO2011/155897
PCT Pub. Date: Dec. 15, 2011

(65) Prior Publication Data
US 2013/0040333 A1 Feb. 14, 2013

Related U.S. Application Data

(60) Provisional application No. 61/353,474, filed on Jun. 10, 2010.

(30) Foreign Application Priority Data

Jun. 10, 2010 (SE) ...................... 1050595

(51) Int. Cl.
*A61M 1/00* (2006.01)
*G01N 33/49* (2006.01)

(52) U.S. Cl.
CPC ............... *A61M 1/00* (2013.01); *G01N 33/491* (2013.01); *A61M 2205/3306* (2013.01)
USPC ..................... 435/29; 435/2; 436/63

(58) Field of Classification Search
CPC .................. A61M 1/029; A61M 1/00; A61M 2205/3306; A61M 2230/00; A61M 2230/20; G01N 33/48; G01N 33/483; G01N 33/49; G01N 33/491; G01N 33/72; G01N 33/726; B01D 39/00; B01D 61/00; B01D 71/00; B01D 2201/00; B01D 2201/16; B01D 2201/204; B01L 9/00; B01L 99/00; Y10S 435/81; A61B 1/00; A61B 5/00; A61B 5/1405; A61B 5/145; A61B 5/1468; A61B 5/1477
See application file for complete search history.

(56) References Cited

U.S. PATENT DOCUMENTS

| 4,863,453 A | * | 9/1989 | Berger et al. ................. 604/415 |
| 6,659,975 B2 | * | 12/2003 | Amano et al. ................. 604/48 |
| 7,282,179 B2 | * | 10/2007 | Iwaki et al. .................. 422/422 |
| 7,521,022 B2 | * | 4/2009 | Konrad ......................... 422/550 |
| 2001/0039030 A1 | * | 11/2001 | James et al. ..................... 435/32 |
| 2007/0284298 A1 | * | 12/2007 | Samsoondar ............ 210/321.62 |
| 2009/0211642 A1 | * | 8/2009 | Lynn ................................ 137/1 |

FOREIGN PATENT DOCUMENTS

| EP | 0552014 A1 | 7/1993 |
| GB | 1283273 A | 7/1972 |
| JP | 57133350 A | 8/1982 |
| JP | 62000838 A | 1/1987 |
| WO | 9623223 A1 | 8/1996 |
| WO | WO 96/23223 | * | 8/1996 | ............ G01N 33/49 |
| WO | WO 9623223 A1 | * | 8/1996 |

OTHER PUBLICATIONS

Definition of "vacuum" and "valve"—Random House Dictionary, Copyright 2013, Random House (online edition).*
Definition of "hydrostatic pressure"—American Heritage Science Dictionary, Copyright 2002, Houghton Mifflin (online edition).*
International Search Report and Written Opinion issued Oct. 14, 2011 in parent PCT/SE2011/050718.

* cited by examiner

Primary Examiner — John S Brusca
Assistant Examiner — Sharon M Papciak
(74) Attorney, Agent, or Firm — Jeffrey S. Melcher; Manelli Selter PLLC

(57) ABSTRACT

The present invention relates to a device for visual detection of hemolysis in a whole blood sample, comprising at least one visible detection compartment and a transfer passage connected to said visible detection compartment, said transfer passage being arranged to permit transfer of a volume of plasma from said sample to said detection compartment and wherein said transfer passage further is arranged with a separation device (4) for separating plasma from blood cells within said whole blood sample before said plasma reaches the detection compartment, wherein said device is arranged with subpressure means providing a subpressure inside said detection compartment for generating a force urging said volume of plasma to be transferred from said whole blood sample to said detection compartment through said transfer passage and via said separation device.

10 Claims, 13 Drawing Sheets

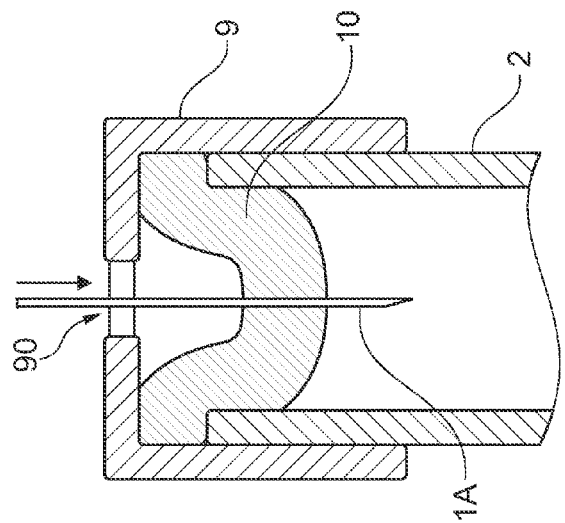
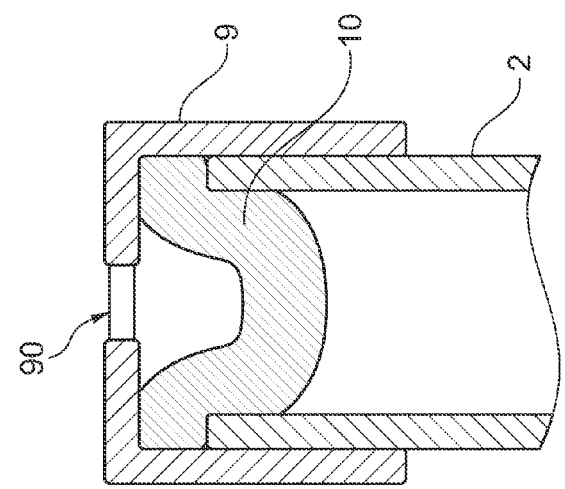
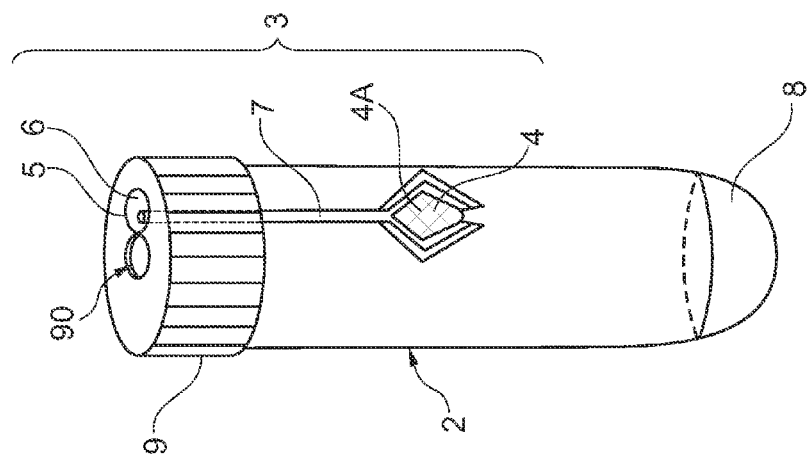
Fig. 2c
Fig. 2b
Fig. 2a

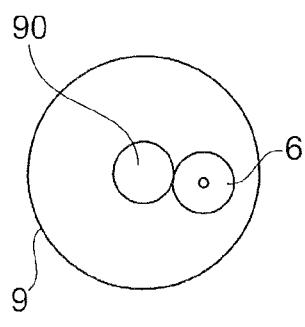
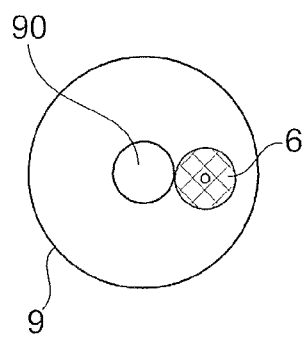
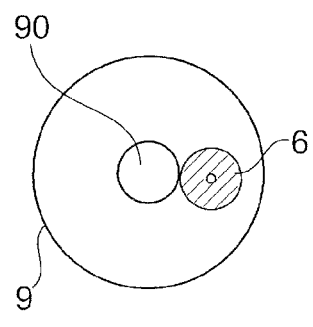
Fig. 4a     Fig. 4b     Fig. 4c
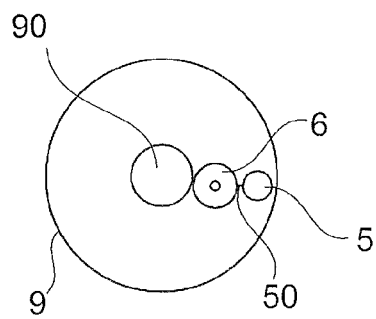
Fig. 4d

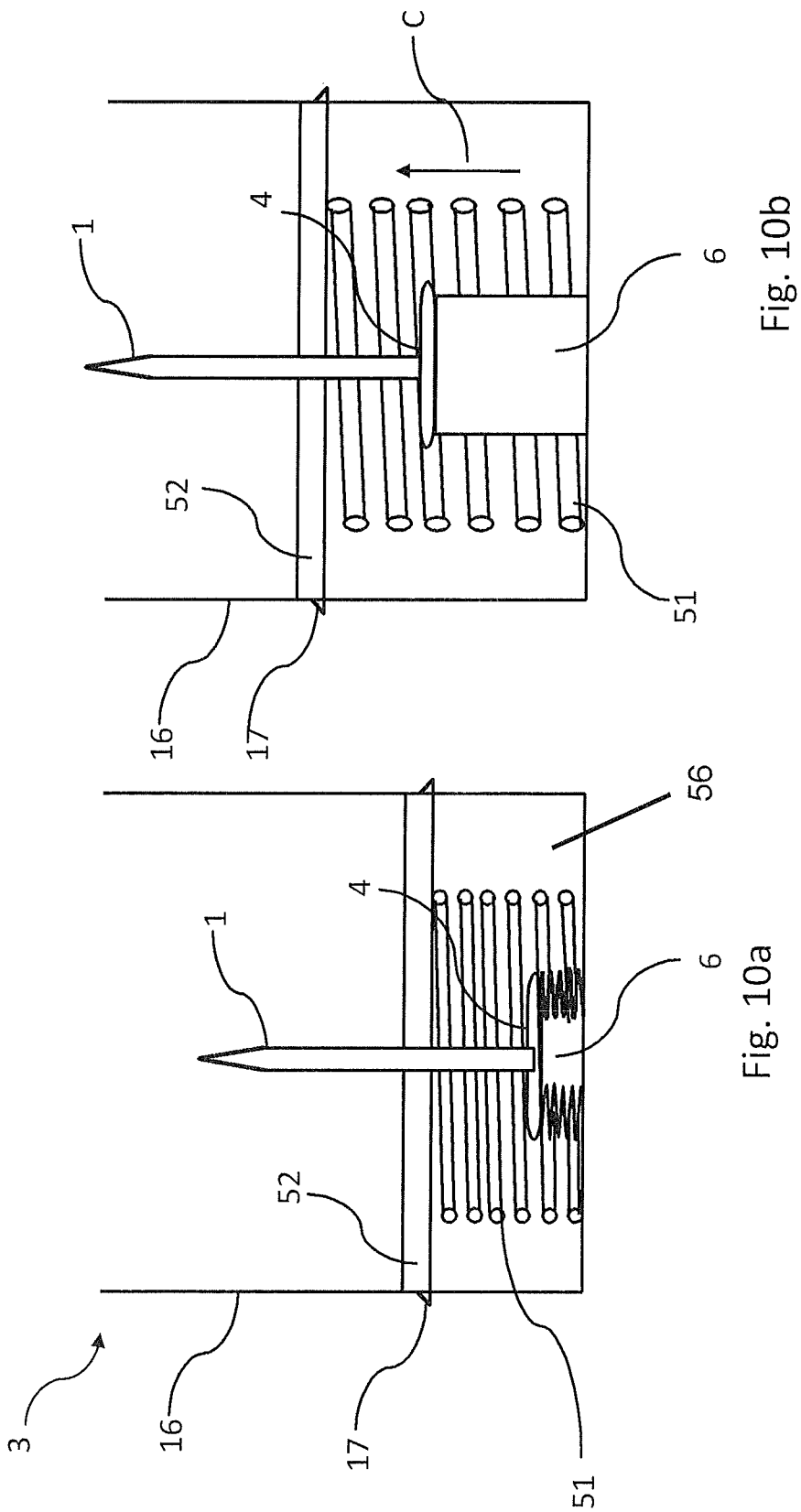

METHOD AND DEVICE FOR VISUAL DETECTION OF HEMOLYSIS

TECHNICAL FIELD

The following invention relates to a device for visual detection of hemolysis in a whole blood sample, comprising a visible detection compartment and a transfer passage connected to said visible detection compartment, said transfer passage being arranged to permit transfer of a volume of plasma from said sample to said detection compartment and wherein said transfer passage further is arranged with a separation device for separating plasma from blood cells within said whole blood sample before said plasma reaches the detection compartment. The invention also relates to a method for visual detection of hemolysis in a whole blood sample.

BACKGROUND ART

Laboratory testing is probably the most common clinical routine performed in modern medical care. Cerebral spinal fluid and urine may be used for
biochemical analysis, however blood is the body fluid mostly used and these tests are highly important diagnostic and prognostic tools in the everyday patient care.

Laboratory testings could be divided into three phases.

The pre analytic phase: all steps before the actual analysis of a sample including patient variables, collection, handling and processing The analytic phase The post analytic phase: test reporting variables Obviously it is of great importance that all three phases are performed correctly since errors could give misleading information to the physicians and therefore jeopardize the well-being of individuals or groups of patients. A majority of the errors seen in laboratory testing occurs in the pre analytic phase, and hemolysis is one of the most significant causes for rejection of specimen. Hemolysis is typically understood as the release of hemoglobin and other intracellular components from erythrocytes to the surrounding plasma, following damage or disruption of the cell membrane. Hemolysis may occur either in vivo or in vitro, and is a most undesirable condition that influences the accuracy and reliability of laboratory testing. Reasons to why hemolysis interferes with multiple biochemical analysis may be e.g. that hemoglobin interferes with the measurements (e.g. spectrophotometric methods), and also that the release of biochemical markers from the broken red blood cells causes false high values of these substances.

Visible hemolysis, as a hallmark of a more generalized process of blood cell damage, is usually not apparent until the separation of serum or plasma has occurred. It is commonly defined as an extracellular hemoglobin concentration of 0.3 g/L (0.0186 mmol/L), resulting in a detectable pink-to-red hue of serum or plasma. Generally a collected blood sample needs to be transferred to a distant department where red blood cells are separated from the plasma or serum, for instance by means of centrifugation, and said hue may be detected and reported to the staff in charge of the patient.

Modern laboratories also objectively assess the degree of hemolysis in every blood sample coming in for analysis. If the hemolysis is substantial enough to cause clinically relevant interference to the analysis the result is not reported and a new samples has to be collected from the patient. Obviously the above described procedures for assessing the validity of the specimen is related to a time delay causing an undesirable situation for the patient as well as leading to circuitous routines.

Alternative detection methods have been suggested, for instance in WO96/23223 which describes a method and apparatus for detecting hemolysis from a blood sample which may be used in a non-laboratory environment. However the detection procedure according to WO96/23223 requires a series of time consuming and inefficient steps leading to a laborious procedure and undesired interruptions.

OBJECTS OF THE INVENTION

It is an object of the invention to provide an improved way of assessing hemolysis in immediate connection to collecting a blood sample, said assessment being possible to perform by a user e.g. in a treatment room without the necessity of a laboratory.

It is a further object of the present invention to provide a rapid way of detecting hemolysis in a whole blood sample, wherein an assessment preferably can be made within one minute, preferably within less than 30 seconds from initiating use of a device according to the invention.

It is a further object of the invention to provide a way of assessing hemolysis with only a very small volume of whole blood sample, preferably between 2-100µl whole blood, preferably resulting in between 1-50µl plasma volume for detection.

It is a further object of the present invention to provide a way of assessing hemolysis which is intuitive and easy to handle, preferably wherein the person collecting a blood sample may perform the steps for detecting hemolysis by using one hand only.

These and still other objects of the invention will become apparent upon study of the accompanying drawings and description of the invention.

SUMMARY OF THE INVENTION

The objects of the invention are achieved by means of a device for visual detection of hemolysis in a whole blood sample, comprising at least one visible detection compartment and a transfer passage connected to said visible detection compartment, said transfer passage being arranged to permit transfer of a volume of plasma from said whole blood sample to said detection compartment and wherein said transfer passage further is arranged with a separation device for separating plasma from blood cells within said whole blood sample before said plasma reaches the detection compartment, wherein said device is arranged with subpressure generating means providing a subpressure inside said detection compartment for generating a force urging said volume of plasma to be transferred from said whole blood sample to said detection compartment through said transfer passage and via said separation device.

Providing of a subpressure inside the detection compartment will lead to the advantage of efficient plasma separation through a separation member (e.g. a filter) and of reliable transfer of the resulting plasma sample into the detection compartment.

Since hemolysis is visually detectable in serum or plasma the arrangement according to the invention provides an opportunity for the person collecting a sample to, immediately upon entry of the plasma into the detection compartment, visually determine if a clinically significant hemolysis is present in the sample before the tube containing the sample is sent to the laboratory. Such determining of hemolysis may be done by merely observing the hue of the plasma portion inside the detection compartment (i.e. if the plasma is amber no hemolysis has occurred, but if the plasma is light pink to red hemolysis can be suspected and a new blood sample should be collected).

It is understood that a "user" may refer to any person operating the device for detecting hemolysis and may include e.g. a medical practitioner, a health care provider and/or a laboratory personnel or a veterinarian.

In the following description "blood collection arrangement" shall be understood to include (in a non-limiting sense) a collection tube, a blood collection tube, a conventional tube, a blood bag and a capillary tube. Furthermore, a test tube may refer to a) a collection tube, a blood collection tube, a conventional tube and vice versa.

In case of rejected specimen due to occurred hemolysis in the collected blood sample the invention will also enable for, possibly even prior to the sample equipment is removed from the patient, collection of a new sample more suitable for analysis. This leads to many advantages. The situation for the patient will be considerably improved since the risk for required recollection of a blood sample is reduced when using the inventive detection device. The time delay caused by the laboratory hemolysis testing is eliminated leading to quicker processing of blood sample analysis which of course means more rapid delivery of results/diagnosis as well as higher success rate in following sample analysis and cut costs.

Thanks to the device according to the invention there is provided a way of detecting hemolysis in a collected blood sample which comprises very few steps, which is easy and intuitive, which is quick, requires only a small sample volume and which can be performed using one hand only in immediate connection (e.g. bedside) to a patient.

According to one aspect of the invention said detection compartment and said separation device are arranged within a housing, and said transfer passage comprises a needle element having a first end portion for penetrating the sealing member of a blood collection arrangement (e.g. a collection tube, a blood bag or a capillary tube) and a second end portion arranged at the housing and in connection to said separation filter. It is to be understood that "in connection to" here shall be interpreted in a way that the needle element is positioned with its second end portion, and the mouth at the corresponding second end portion, positioned adjacent to the separation filter so that any whole blood passing through the needle upon exit the needle will proceed onto and through the filter. Together with said subpressure means this arrangement allows for a quick and easy way of transferring a whole blood sample from inside a collection tube via said needle element to the detection device according to the invention. Preferably, a subpressure may be generated inside the detection compartment substantially simultaneously to penetration by means of said needle element, or as an immediate consecutive step, so that whole blood from the e.g. collection tube will get drawn through the needle, and plasma transferred through the separation device and further into the detection compartment directly upon that the needle penetrates the sealing member of the collection tube and contacts the whole blood to be tested. Subpressure driven transfer of the sample is advantageous if the whole blood to be tested is provided in a conventional vacuum-type collection tube (i.e. which collects a blood sample from a patient by means of vacuum). In such a case, the collection tube may still contain a certain vacuum even after collection of a blood sample from a patient, for instance in case less whole blood than the intended volume has been collected in the collection tube. Evidently any remaining vacuum may hamper easy withdrawal of blood from such a vacuum-type collection tube. Thanks to said internal generation of subpressure the detection device according to the invention provides a way of secure and efficient collection of plasma even from a vacuum-type collection tube. Since a very small volume of plasma is required for detection of hemolysis a slight subpressure is enough for both overcoming any remaining vacuum inside a collection tube and for urging the needed volume to become transferred through the filter and into the detection compartment.

Said subpressure means may correspond either to a prearranged subpressure inside the detection device, which is activated upon use of the device or to a subpressure generating device whereby a subpressure can be created by a user. For instance, according to one aspect of the invention said visible detection compartment comprises or is connected to a subpressure generating device for manually creating a subpressure inside the detection compartment leading to the upcome of a subpressure force urging a portion of plasma to be drawn through the transfer passage, through said separation device and further entering into said detection compartment. Such subpressure generating device may be in the form of an external device (e.g. a pump) or an air-displacing unit integrated with the device and for instance comprising a valve, such as a check valve, so that air may be forced to exit the compartment but is prevented from entering again hereby leading to generation of a subpressure inside the compartment. A checkvalve may lead the air to exit out of the device, however preferably not through the transfer passage. Air displacement may be achieved e.g. by manually pressing air to exit from the detection compartment, as will later be described in more detail.

According to one aspect of the invention said subpressure generating device is manually maneuvered, so that a practitioner may easily activate the subpressure generating device immediately upon use of the detection device. By creating a subpressure inside the detection compartment when the transfer passage is in contact with a blood sample a small portion of blood plasma can be urged to enter the visible detection compartment through the separation device, and hemolysis may subsequently be detected e.g. by evaluating the hue of the plasma.

According to one aspect of the invention said transfer passage is provided with a transfer channel creating a distance between the separation device and the detection compartment. This provides the advantage that possible red color on the separation device resulting from the separated red blood cells will not interfere with the visual assessment of the color of the plasma inside the detection compartment.

According to yet another aspect of the invention said detection device is an integrated part of a blood sample collection tube, said tube having open and closed ends wherein said open end is provided with a sealing member arranged to seal said tube. Such an embodiment would provide an easy way of detecting hemolysis in a collected blood sample since visual inspection of a plasma sample would be possible substantially directly when blood has entered into the collection tube. According to this embodiment said transfer passage is arranged to permit the transfer of a portion of plasma from a whole blood sample collected in said blood collection tube to said detection compartment, wherein the detection compartment is visibly arranged on the tube, for instance integrated within the lid portion thereof. A separation device may be positioned at the inside as well as at the outside of such blood collection tube.

According to yet another aspect of the invention the detection device comprises a transfer passage, e.g. a transfer channel, located inside a blood collection tube and arranged so that a first end thereof may be brought into contact with a blood sample volume collected therein. A second end of the transfer passage is connected to the detection compartment, and in between the first end and the detection compartment there is arranged a separation device. When a portion of the blood sample inside the collection tube is caused to move through the transfer passage (by means of subpressure inside the detection compartment) it will become filtered through said separation device before reaching the detection compartment so that only blood plasma from the blood sample will enter therein.

According to yet another aspect of the invention said separation device is a separation filter (or separation membrane) arranged to separate plasma from the cellular components of whole blood sample without lysis. It is understood that the filter may be any known conventional filter or membrane which meets the separation requirements of the present equipment, including membranes made from synthetic as well as natural polymers, preferably but not necessarily a hydrophilic membrane. According to one embodiment the separation filter is asymmetric meaning the filter pores have varying sizes. The filter may have any suitable geometry or shape, e.g. being substantially flat or being three dimensional, e.g. cylinder shaped. The size and/or volume of the filter depend on the filter type as well as the specific plasma volume that is to be separated there through.

According to another aspect of the invention said cross sectional filter area of said filter is substantially larger than the cross sectional area of said transfer passage.

According to another aspect of the invention the separation device is a separation column comprising a gel or beads arranged to separate plasma from whole blood.

Thanks to the separation device (e.g. filter or column) the whole blood is efficiently separated from the plasma which may subsequently become easily analyzed once inside the visible detection compartment.

According to yet another aspect of the invention said at least one detection compartment is arranged with chemical means for direct visual detection. The chemical means for visual detection may lead to a change of color in case hemolysis has occurred whereby it is permitted for safer and more reliable test results and easier evaluation, especially in case there is only a slight hue of pink where correct assessment by just looking at the color of the plasma might prove to be difficult.

BRIEF DESCRIPTION OF THE DRAWINGS

The invention will now be described more in detail with reference to the appended drawings, wherein:

FIG. 2a is a schematic perspective view of a blood sample collection arrangement with a detection device according to another embodiment of the present invention, FIGS. 2b-2c show schematic cross sections of a top-portion of a sealed conventional blood collection tube, FIGS. 4a-4c illustrate in a schematic way different outcomes of tests with an arrangement according to the present invention, FIG. 4d is a top view of a blood sample collection arrangement according to one embodiment of the invention, FIGS. 10a-10b show an example of a subpressure means and a detection device according to one embodiment of the invention.

DETAILED DESCRIPTION OF THE INVENTION

The foregoing aspects and many of the attendant advantages of this invention will become more readily appreciated as the same become better understood by reference to the following detailed description, when taken in conjunction with the accompanying figures. Further, the description, and the examples contained therein, are provided for the purpose of describing and illustrating certain embodiments of the invention only and are not intended to limit the scope of the invention in any way.

Figure 1B:
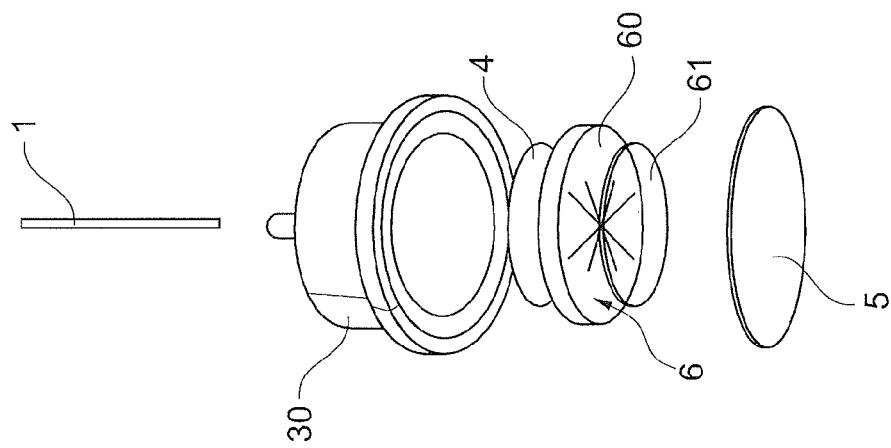
FIGS. 1a-1e illustrate a blood sample collection arrangement with a detection device according to one embodiment of the present invention.
Figure 1A:
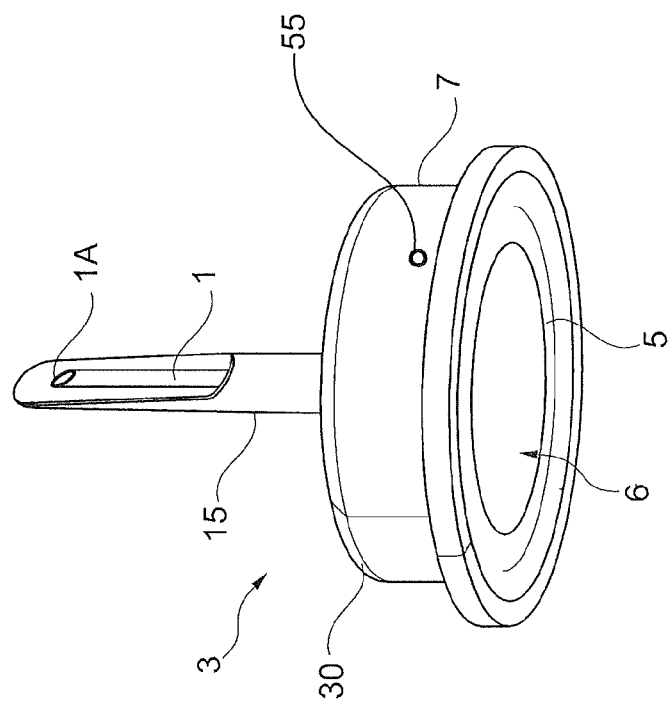
Figure 1D:
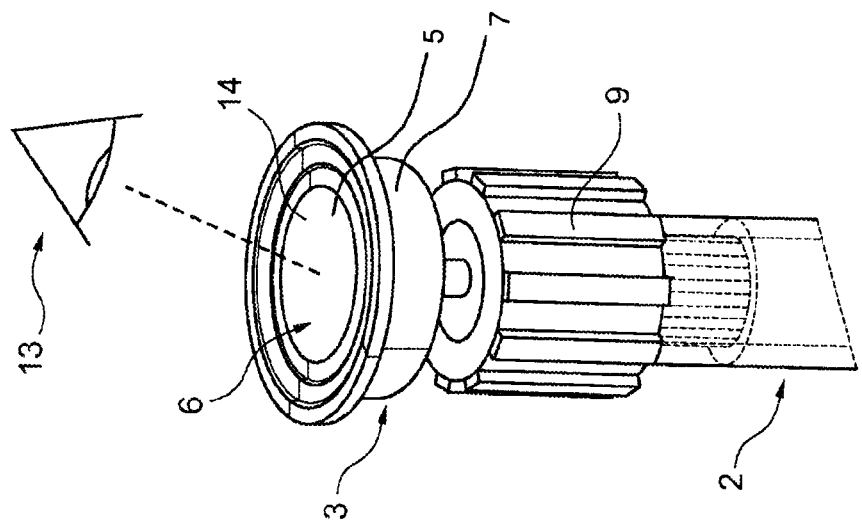
Figure 1C:
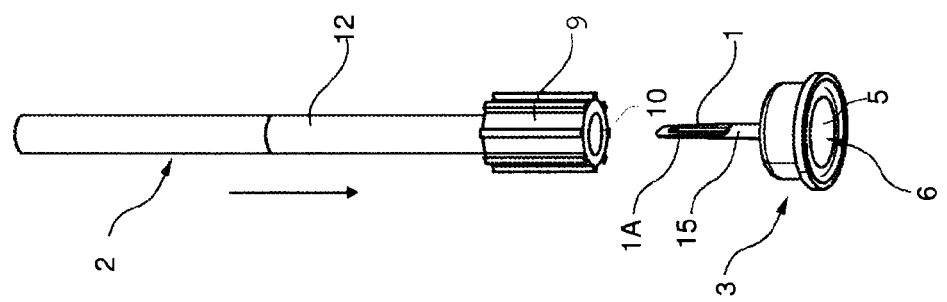
Figure 1E:
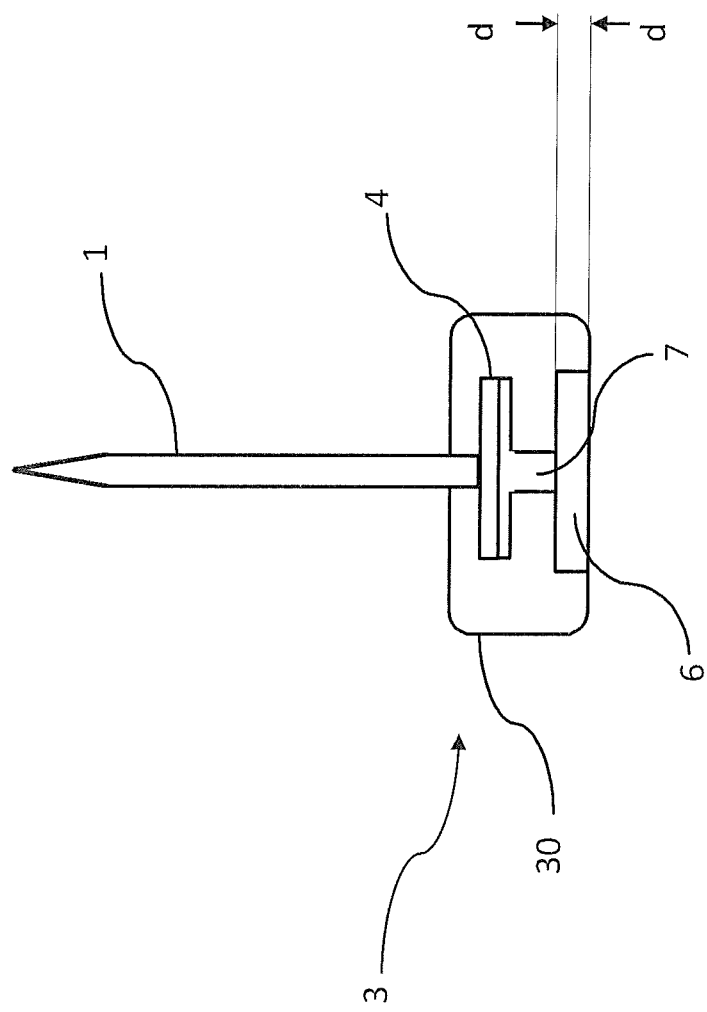

FIGS. 1a-1e show a preferred embodiment according to the invention. Herein FIGS. 1a-1b schematically illustrate a detection device 3 arranged to visually indicate hemolysis in a blood sample 12, FIG. 1a showing a perspective view of the assembled device 3 and FIG. 1b showing an exploded view of the device 3 according to FIG. 1a. FIGS. 1c-1d further show the principle for performing a quick instant testing of hemolysis of a blood sample 12 in a collection tube 2, by means of a detection device 3 according to the present invention. FIG. 1e shows in a simplified and schematic way a cross section of a detection device 3 according to one exemplary embodiment of the invention.

Referring firstly to FIGS. 1a-1b, in its first end said detection device 3 comprises a needle element 1 which in non-operational mode is preferably provided with a protecting cover 15 (e.g. made of rubber). The needle 1 has a first part 1A creating a tip, and a second end being arranged at a housing 30 of the device 3 and in connection to a separation device 4, preferably a separation filter, arranged to be brought into contact with a blood sample 12 and permit passage of free hemoglobin and stop passage of red blood cells thus allowing for the passage of blood plasma 14. A transfer channel 7 provides for further passage of plasma from the filter 4 to a visible detection compartment 6 preferably positioned at the second end of said detection device 3, said second end being opposite to said first end. The needle 1 and the transfer channel 7 together forms a transfer passage 1, 7 for the sample.

Preferably the filter surface which is arranged to contact the blood sample is substantially much larger (e.g. at least 10 times) than the cross sectional surface of the needle 1 cross section, in order to eliminate risk for clogging of the filter 4.

The transfer channel 7 may correspond to a channel-like portion as shown in FIG. 1*e*, however it is also possible to arrange the filter 4 and the detection compartment 6 substantially adjacent to each other, however separated by some type of separation surface 60 in which case said transfer channel 7 shall be interpreted as a mere interface between the filter and the detection compartment. One possible design is seen in FIG. 1*b*. Between the separation device 4 and the detection compartment 6 there may be arranged a distribution surface 60 constituting the bottom portion of the detection compartment 6. The distribution surface 60 is preferably provided with passages (e.g. channels, openings, pores, slits or any other suitable passage type) for allowing passage of plasma from the filter 4 and at the same time leading to a plasma distribution over the bottom of the detection compartment 6 so that the plasma to be examined is evenly distributed inside the chamber 6. An even plasma distribution will lead to safer assessment of hemolysis. The distribution surface 60 is preferably arranged to not allowing any passage of color (i.e. red color from filtered blood cells), and may for this reason for instance be formed by a non-transparent material which blocks any light from passing/shining through the body 60.

Preferably the side of the distribution surface 60 which is intended to face the detection compartment 6, and which will correspond to the background surface of the detection compartment 6, has a white color for the purpose of providing a contrast and facilitating color assessment of plasma.

According to one embodiment said detection compartment 6 is arranged with chemical means for direct visual detection, meaning that a reagent/reagents may be deposited inside the detection compartment 6 which reacts with hemoglobin and produces a color for indicating if hemolysis has occurred.

The device 3 may further comprise a transparent hydrophilic tape 61 for facilitating transfer of plasma into the detection compartment 6. For the same reason (i.e. facilitate plasma transfer) the surface of said distribution surface 60 may comprise a hydrophilic surface treatment such as coating, surfactant or plasma surface treatment for improving wetting and plasma distribution.

The detection compartment 6 is preferably covered by a transparent, resilient membrane 5, preferably which is compressible, for example made of silicone, which allows for a user to visually observe the inside of the detection compartment 6. Preferably but not necessarily said detection compartment 6 comprises a valve 55 such as a check valve arranged to allow for air passage out of the detection compartment 6 and prevent air passage into the detection compartment, wherein compression of the compressible membrane cover 5 will lead to exit of air through the valve 55 and wherein the membrane cover 5 is arranged to strive to retake its original shape after having been compressed. After having been compressed and forcing to exit out of the detection compartment 6 the membrane 5 will try to retake its original unaffected shape, at the same time generating an underpressure inside the detection compartment 6. Hereby the resilient cover membrane 5 may contribute to generating a subpressure inside the detection compartment 6 for achieving plasma separation and transfer of sample plasma into the detection compartment 6 (see further e.g. FIGS. 10-11).

In FIG. 1*c*-1*d* there is illustrated one preferred use of a detection device 3 according to one embodiment of the invention. The device 3 is placed vertically on a surface with the needle 1 pointing upwards as shown in FIG. 1*c*, said needle being protected by the protecting cover 15. Possibly said device 3 may be placed inside some supporting holding structure (not shown) safeguarding that it is kept in a rightful position and doesn't fall or move. Next a blood sample collection arrangement 2, here in the form of a conventional collection tube 2, containing a blood sample 12 to be tested is provided. Typically such a collection tube 2 is constructed of glass material or injection molded plastic such as polypropylene, polystyrene or any other suitable polymer. Preferably the collection tube 2 has an elongate shape with a circular wall, having one closed end and one open end defining a chamber therein for receiving sample of a collected fluid (e.g. blood 12) from a patient. The open end is tightly sealed with a resilient sealing member 10 (seen in FIGS. 2*b*-2*c*). The sealing member 10 (e.g. a sealing plug) can be made of rubber or some other suitable resilient material, and is disposed at the open end of the tube 2 to close the chamber and hermetically seal the interior of the tube. Further, the open end of the 2 is protected by a protecting lid 9 attached onto tube 2 and over the sealing member 10. The protecting lid 9 comprises a central opening 90 intended for passage of a needle 1 arranged to penetrate the sealing member 10.

As shown in FIG. 1*c* said tube 2 containing a blood sample 12 is positioned upside down, so that its open end with the lid 9 and the sealing plug 10 is facing the needle tip 1 A of the detection device 3. Next, the collection tube 2 is applied onto the detection device 3 by means of pushing the tube onto the device 3 in such a way that the needle 1 pierces through and penetrates the sealing member 10. Applying the collection tube onto the detection device 3 results in that the protecting cover 15 is pushed aside/gets removed by the movement. Having pierced through the seal 10 the needle tip 1 A reaches the blood sample 12, and a portion of said blood sample may transferred into and through the needle 1, further onto the filter body 4 as a consequence of a subpressure inside the detection compartment 6. Upon reaching the filter body 4 the whole blood sample will wetten the filter 4 so that it becomes impermeable to air hereby sealing the interior detection compartment 6 of the detection device 3. In order to ensure passage of whole blood from the tube 2 through the needle said device 3 is arranged with subpressure means providing a subpressure inside said detection compartment 6 for generating a force urging said volume of plasma to be transferred from said whole blood sample 12 to said detection compartment 6 through the needle 1 and transfer channel 7 respectively, and via said separation device 4. Various possibilities of accomplishing a subpressure inside the detection compartment 6 exist, for instance the device 3 may be delivered with a prearranged subpressure inside the device 3 arranged to be activated upon use, or the device 3 may comprise an integrated subpressure generating device connected to the detection compartment 6. One way of achieving a subpressure inside the detection compartment 6 is to provide a check valve 55 combined with a air-displacing member 5 in connection to the detection compartment 6. For instance as can be seen in FIGS. 1*a*-1*d* the detection compartment 6 is covered by a flexible/resilient membrane 5 which is possible to compress. By connecting the detection compartment 6 to a check valve 55 it is possible to force air to exit from the compartment 6 by gently pressing on the membrane 5. When releasing the membrane 5, removing the applied pressure, it will retain its original uncompressed shape thereby giving rise to a subpressure inside the detection compartment 6 which will initiate plasma separation process. Compression of the membrane 5 may be done in any suitable way, e.g. by manual pressing or by pushing the device 3 with the membrane 5 against a surface. It is also conceivable that the detection device 3 comprises a lid (not shown) which initially keeps the membrane 5 in a compressed state, where removal of such lid allows for the bellow to return to uncompressed state thereby generating a subpressure which drives plasma separation through the filter 4.

Other subpressure means for driving plasma separation will later be described in more detail, for instance in FIGS. 10-11.

Subsequently to having passed through the filter 4, plasma 14 will be transferred via the transfer channel 7 and enter into a visible detection compartment 6 at one end of the detection device 3. As shown in FIG. 1*d*, the user 13 may turn the tube 2 which is still connected to the detection device 3, for visually inspecting the detection compartment 6 and the plasma 14 therein hereby being able to determine whether or not hemolysis has occurred in the blood sample 12: if the plasma is amber no hemolysis has occurred, but if the plasma is pink hemolysis can be suspected and the blood sample 12 should be replaced by a new one. In order to simplify assessment of hemolysis the device may be provided with a color reference for comparison with the sample plasma, e.g. showing a cutoff color wherein if the plasma color is darker than the reference hemolysis can be suspected and vice versa. Such color reference may for instance be arranged next to the visible detection compartment on the top portion of the device 3.

If no hemolysis has occurred the detection device 3 is removed from the tube 2 and discarded as waste material, and the tube 2 with the sample 12 can be passed on to further analysis.

A use wherein said detection device 3 initially is positioned with its needle element 1 pointing upwards, as described in connection to FIG. 1*c*-1*d*, may lead to advantages that the transfer and separation of plasma can be done very quickly, substantially in one movement and using one hand only, however the invention is not to be limited to such a use. The skilled person understands that it is also possible to apply a detection device 3 onto an upright positioned collection tube, with its sealing member facing upwards. In such a case, however, a user will position the tube containing the whole blood to be tested in such a way that the needle element 1 is brought into contact with the whole blood at the point when subpressure is generated inside the detection compartment 6 for safe transfer of plasma into the detection compartment.

Although one preferred use of the detection device 3 is to detect hemolysis in whole blood sample inside a collection tube 2 (as previously described) the skilled person will understand that other uses are also possible, such as detecting hemolysis inside capillary tubes and/or blood bags. Thus the skilled person will also understand that although a "needle element" conventionally is made of steel material the needle element referred to in this description is not to be limited thereto. In certain circumstances it might suffice with a needle in some other hard material suitable for the specific function, such as hard plastic or glass.

FIG. 1*e* illustrates a cross section of a simplified schematically drawn detection device 3 according to one embodiment of the invention, here positioned with its exposed needle member 1 (i.e. here shown without cover 15) pointing upwards. The needle 1 is arranged with one lower end connected to the housing 30 and is positioned in connection to a separation device 4 (e.g. filter 4) so that whole blood exiting the needle 1 will proceed onto the separation filter 4. A transfer channel 7 creates a distance between the separation device 4 and the detection chamber 6, which detection chamber 6 is positioned at the side of the device 3 which faces downwards in FIG. 1*e*. A transfer channel 7 creating said distance between the separation device 4 and the detection chamber 6 may sometimes be advantageous, for instance in order to prevent red color from the filter 4 to disturb color assessment of the plasma. However the skilled person understands that other designs are also possible where the separation device 4 and the detection chamber 6 are arranged substantially adjacent to each other, in which case it is advantageous to provide a shielding member, such as e.g. a distribution surface 60 (described in FIG. 1*b*), for preventing separated red blood cells from interfering with the plasma color assessment. In such an embodiment said transfer channel 7 is represented by an interface or the mere passage of plasma from the filter 4 to the detection compartment 6. Preferably the detection compartment 6 is arranged with a depth d between 0.05-5 mm. The diameter of the detection compartment 6 is preferably adapted to the volume of plasma which the device 3 is intended to detect. Preferably the detection device 3 is arranged to filter a volume of between 2-100 whole blood resulting in about between 1-60µl plasma for visual observation.

The detection compartment 6 may be arranged with chemical means for direct visual detection. Such chemical means for visual detection may lead to a change of color in case hemolysis has occurred whereby it is permitted for safer and more reliable test results and easier evaluation. For instance a common method for colorimetric detection of hemoglobin is Drabkin's reagent, which consists of potassium cyanide. Other alkali cyanides as well as ferricyanides could also be used in such an assay. Further examples of chemical means for visual detection may include colorimetric methods making use of the peroxidase activity of hemoglobin, based on a chromogen such as benzidine compounds with peroxides as substrate. The chemical means (reagents) may be deposited inside the detection compartment 6 either as in dried form or as wet reagent, or as a combination of dry and wet reagents.

The described method for detecting hemolysis using the detection device 3 according to anyone of FIGS. 1*a*-1*e* can be performed very easily, quickly and in direct connection to taking a blood sample 12 from a patient. An operator 13 needs only one single hand for performing all the necessary steps for detecting hemolysis, no preparatory steps are required, and the time from applying a test tube 2 on a detection device 3 to readout of the result is extremely short, preferably less than 1 minute, more preferred less than 30 seconds.

Referring now to FIG. 2*a* there is shown a schematic perspective view of a blood sample collection arrangement 2 with a detection device 3 according to another exemplary embodiment of the invention. Herein the detection device 3 is integrated with a blood collection tube. The blood sample collection arrangement is preferably a conventional collection tube 2, having one open end tightly sealed with a resilient sealing member 10, seen in FIGS. 2*b*-2*c* which schematically show a cross section of a sealed open end of a conventional collection tube 2, FIG. 2*c* showing an arrangement penetrated by a needle 1A. The sealing member 10 disposed at the open end of the tube 2 closes the chamber and forms a seal capable of maintaining a pressure differential between atmospheric pressure and pressure less than atmospheric pressure inside chamber of tube 2.

Conventionally when collecting a blood sample from a patient a blood tube holder (not shown) comprising a needle element 1 with a distal end 1 A and a proximal end (not shown) is used. The proximal end of said needle 1 is first introduced into a patient to draw blood, and the distal end 1 A is subsequently inserted into a blood collection tube 2 like the one shown in the appended figures via the hole 90 in the protecting lid 9, further penetrating said sealing member 10. In case the collection tube 2 is vacuum-type, blood will be drawn into the container 2 via the needle 1 by means of the low pressure inside the tube 2.

In the bottom of the collection tube 2 there is preferably an additive 8 for preventing coagulation, for instance lithium heparin, EDTA, citrate or any other suitable anticoagulant.

The blood sample collection arrangement according to one embodiment of the invention is provided with a detection device 3, which in the embodiment seen in FIGS. 2a-2c is integrated with the tube 2 and which is arranged to visually indicate hemolysis within a blood sample inside said collection tube 2.

The detection device 3 according to the exemplary embodiment in FIG. 2a comprises one portion which is arranged inside the tube 2 to contact a blood sample 12 collected in the tube 2, and one portion visibly arranged at the top of the protecting lid 9. The detection device 3 comprises a separation device, preferably a separation filter 4, arranged to be brought into contact with a blood sample and permit passage of free hemoglobin and stop passage of red blood cells, meaning it is permeable to plasma which may thereby pass through the filter 4 and proceed through a transfer passage 7. In a detailed form the transfer passage of the exemplary embodiment in FIG. 2a includes a transfer channel 7. The plasma further enters into a visible detection compartment 6 which is connected to a subpressure generating device 5. For instance the subpressure generating device 5 may be in the form of a resilient bellow-member 5, which in FIG. 2a comprises the shape of a half-sphere and covers said detection compartment 6 and is visibly located on top of the protecting lid 9. Generation of a subpressure inside the detection compartment 6 may be achieved by means of compressing the bellow member 5 thereby displacing an air volume which may exit the detection compartment 6 e.g. via a check valve. Compression of the bellow 5 may be done in any suitable way, e.g. by manual pressing or by pushing the bellow against a surface. It is also conceivable that the detection device 3 comprises a lid which initially keeps the bellow 5 in a compressed state, where removal of such lid allows for the bellow to return to uncompressed state thereby generating a subpressure which drives plasma separation through the filter 4.

According to the embodiment shown in FIG. 2 the bellow member 5 is transparent so that the detection compartment 6 is readily observable, however other modifications are also conceivable as will be seen for instance in FIG. 4d.

Figure 5A:
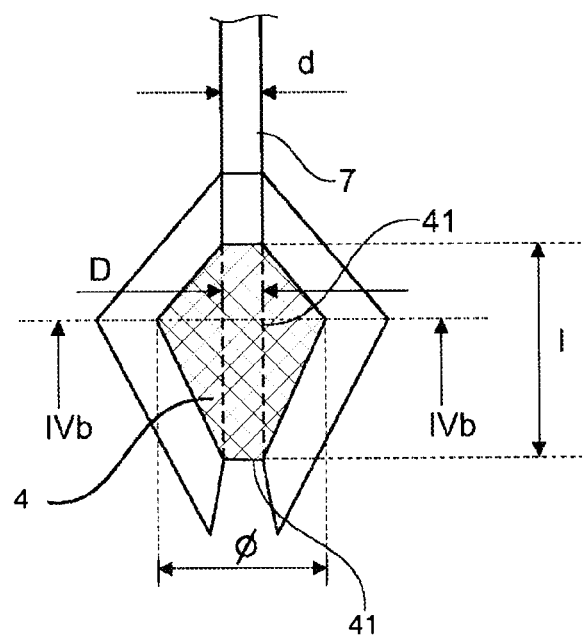
FIG. 5a is a schematic view showing a detail of the detection device according to one embodiment of the present invention.
Figure 5B:
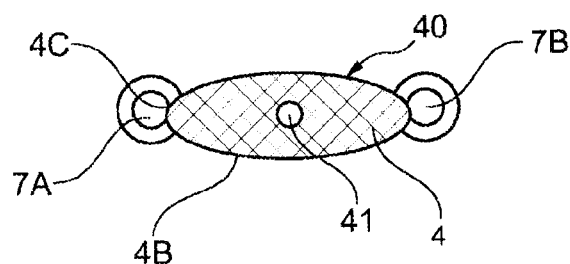
FIG. 5b is a view taken along the line IVb-IVb in FIG. 4a, FIGS. 5c-5d show schematic views of a filter arrangement according to one embodiment of the present invention, is a schematic side view of a blood sample collection arrangement with a detection device according to another embodiment of the present invention.

Preferably the filter surface 4A which is arranged to contact the blood sample is substantially much larger (e.g. at least 10 times) than the cross sectional surface of the transfer channel 7, in order to eliminate risk for clogging of the filter 4. In FIGS. 5a-5b there is shown one of many possibilities to achieve the latter. Here the filter 4 has a body 40 of a flattened rectangular shape, with an outer impermeable surface 4B and a central hole 41 protruding from a lower edge, a substantial distance (at least 50% of its length) into the body 40, thereby presenting a cylindrical filter surface 4B ($=D*\pi*1$) which may be substantially larger than the cross sectional surface ($=d*d*\pi/4$) of the transfer channel 7 for safeguarding efficient generation of high quality plasma from whole blood sample. The filter body 4 is connected to the channel 7 by means of two transfer channel leg portions 7A, 7B, which via permeable side edges 4C of the filter body 40 are in fluid communication with the inner filter surface 4A of the filter 4. In the given example blood will enter via the central hole 41 at the lower edge of the filter 4 and plasma will pass through the filter body into out through the transfer channel leg portions 7A, 7B and will be drawn up through the transfer channel 7 in direction indicated with arrow B as a consequence of generated subpressure according to previously described.

As is obvious to a person skilled in the art it is possible to provide the lower edge of the filter 4 with another channel/capillary member (not shown) arranged to transfer a blood portion from the blood sample 12 to the central hole 41.

Figures 5C, 5D:
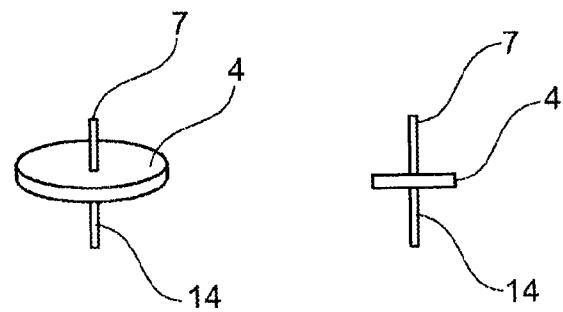

In FIGS. 5c-5d there is illustrated yet another possible principle regarding the alignment of a filter/membrane 4 for separating plasma from a blood sample, where the above mentioned preferred requirement of providing a substantially larger filter surface 4A compared to the cross sectional surface of the transfer channel 7 is fulfilled. FIG. 5c shows a perspective view of the filter arrangement according to the example and FIG. 5d shows a side view thereof. In this embodiment the filter 4 comprises a substantially flat body extending substantially perpendicular in relation to the upper transfer channel 7, and is provided with a lower channel 14 for transporting a portion of whole blood sample 12 to the separation filter/membrane 4, wherein blood plasma is separated from blood cells in the sample 12 before it reaches the transfer channel 7. The size of the filter 4 depends on the sample volume which it is intended to filter, as is known per se.

The detection compartment 6 may contain reagents for colorimetric reaction with free hemoglobin causing change of color within the wavelength spectrum which is visible to the human eye.

In addition to shielding the detection compartment the bellow member 5 provides a subpressure generating device for providing a subpressure force arranged to cause a portion of plasma from said whole blood sample 12 to be drawn into said detection compartment 6 via said passage. The bellow 5 is preferably transparent so that a practitioner may readily observe the detection compartment 6 and any content therein. Further, the bellow-member is preferably made of a flexible, resilient material which may be compressed by means of manual gentle pushing but which will retake its original shape upon release. Moreover, the material of the bellow member 5 is preferably arranged to tolerate the pressure difference inside and outside the collection tube 2, meaning it will not rupture or break due to the initial under pressure inside the collection tube 2 before collection of blood sample 12. The bellow member 5 is preferably made out of a resilient material such as latex, rubber (natural or synthetic rubber) or any other suitable elastomeric material. The skilled person understands that configurations other than a "bellow shape" are possible, and that other types of subpressure generating devices may also be used, for instance a resilient cover 5' as shown in connection to the embodiment in FIG. 9a-b.

Subpressure may be generated in the following way. When compressing the bellow member 5 the air volume therein will be forced to be displaced, e.g. by means of exiting the inside of the bellow via a check valve. Upon releasing the bellow member 5 it will regain its original shape and air is therefore urged to enter the bellow 5, whereby a temporary subpressure is generated inside the bellow member 5 leading to that blood plasma is drawn through the filter 4 and into the detection compartment 6. Thus it is understood that generation of subpressure is achieved by means of air displacement, where such air displacement for instance, but not restricted to it, may be attained by means of said bellow 5.

It is to be understood that subpressure generation by means of a bellow member 5 may be applied for the various embodiments of the detection device 3 described herein, for instance the embodiments shown in FIGS. 1a-1e.

By positioning the different parts of the detection device 3 e.g. in FIG. 2-3 off-centered in relation to the center line of the tube 2, it is avoided that the interacting needle 1 comes into direct contact with any of the parts of the detection device 3, since as is well known in the art the needle 1 is centered in relation to the tube that guides the collection tube 2, upon insertion thereof allow penetration of the needle 1 into the collection tube 2.

The use of an exemplary blood sample collection arrangement comprising an integrated detection device 3 according to the present invention will now be described in more detail, referring mainly to FIGS. 3a-3c. For reasons of clarity the inner sealing device 10 is not shown in FIGS. 3a-3c, however it is to be understood that the distal end 1A of the needle upon introduction into the tube 2 is arranged to penetrate the sealing plug 10 positioned between the lid 9 and the tube 2 as shown in FIGS. 2b-2c.

Figure 3A:
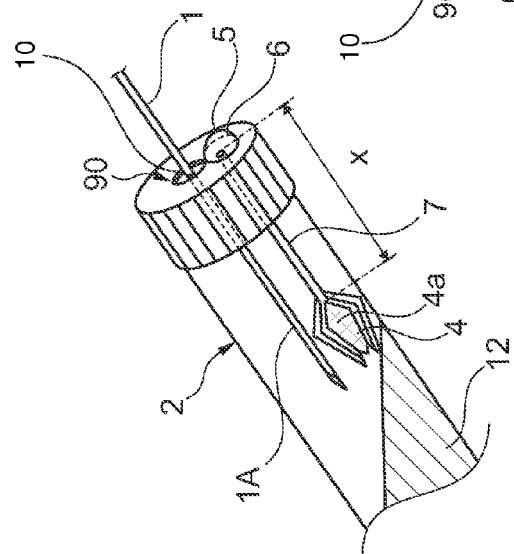
FIGS. 3a-3c illustrate the use of an arrangement according to the present invention.

As seen in FIG. 3a a seal 10 of a blood sample collection tube 2 is penetrated by the distal end 1A of a needle 1. Prior to insertion of the distal end 1A into the tube 2 the needle is already introduced into a patient through its opposite proximal end (well known per se, and therefore not shown) so that blood 12 is drawn through the needle 1 into the collection tube 2, typically by means of vacuum suction. Said filter 4 of the detection device 3 is positioned with its uppermost end at a distance x from the uppermost end of the tube 2 in order to provide enough space for the distal end 1A of the needle 1. In FIG. 3a is illustrated a situation when a blood sample 12 has been collected through said needle 1 which is seen to have been introduced into the tube 2 via the hole 90 in the protecting lid 9 and the distal end 1A having penetrated the sealing member 10 in order to safely introduce blood with no risk of leakage.

Figure 3B:
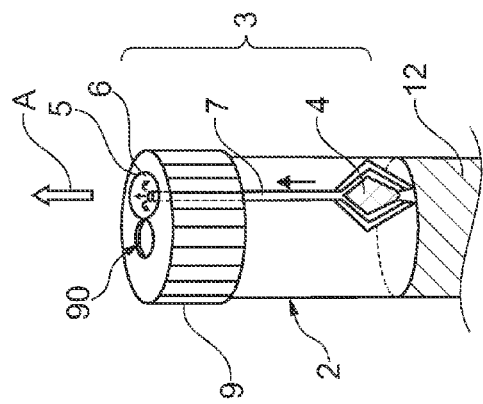
Figure 3C:
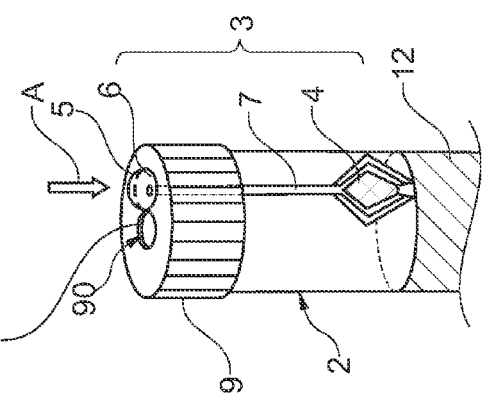

In FIG. 3b the needle 1 has been removed, the sealing member 10 (see FIG. 2b) safeguarding further sealing of the tube 2, and the test tube 2 is moved to a position where the blood sample 12 may get into contact with the separation filter 4 of the detection device 3. Next the sample collector presses the bellow member 5 downwards as indicated with arrow A. Once letting go of the bellow member, indicated in FIG. 3c with arrow A, the bellow member retains its uncompressed shape and a subpressure is hereby generated inside the detection device 3 so that blood plasma is urged through the filter 4 and passes through the transfer passage, e.g. transfer channel 7, into the visible detection compartment 6 arranged at the upper portion of the test tube 2 whereupon detection of hemolysis in the blood sample 12 may be performed.

Three examples of possible outcomes from the detection are shown in FIGS. 4a-4c, showing a top view of a test tube 2 with protecting lid 9 comprising a central opening 90 and a visible detection compartment 6 according to one embodiment of the invention, which detection compartment is covered by a transparent bellow member 5.

In FIG. 4a there is shown a situation where the plasma which has been collected inside the detection compartment 6 is clear, meaning no hemolysis has occurred and the specimen is valid. In FIG. 4b there is shown a situation corresponding to where the plasma comprises a reddish or pink hue, which would indicate that hemolysis has occurred and that a new blood sample needs to be collected from the patient. In FIG. 4c there is shown an example corresponding to where the detection compartment 6 is provided with a suitable reagent whereby presence of hemoglobin in the plasma above a preset level will lead to a color shift for easier determining hemolysis.

FIG. 4d is another exemplary embodiment according to the invention, wherein the detection compartment 6 and the subpressure generating device 5 are arranged separate from each other and connected via an air channel 50. When activating the bellow 5 and generating a subpressure by means of air displacement, subpressure is transmitted via the air channel 50 and urges plasma to enter the visible detection compartment 6.

Evidently in this embodiment the bellow member 5 may or may not be transparent.

Figure 6:
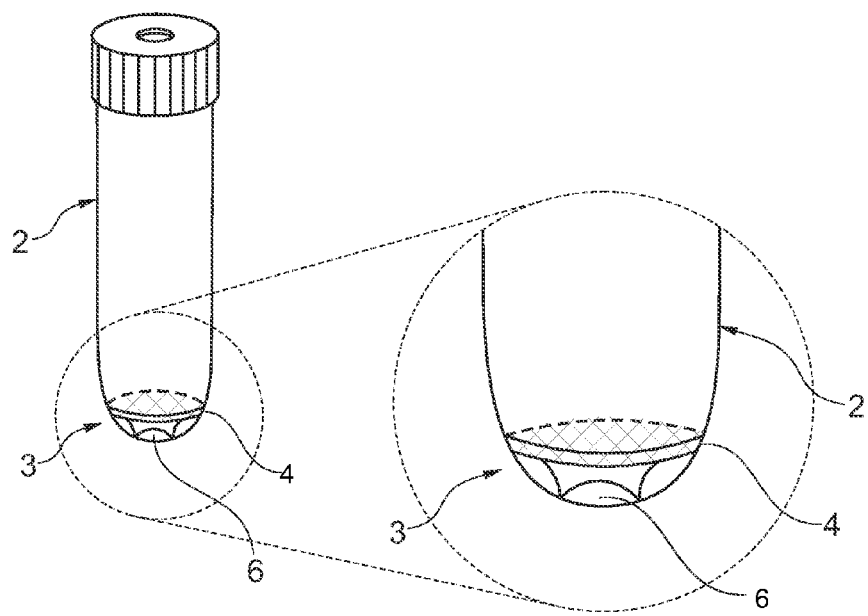
FIG. 6 is a schematic side view of a blood sample collection arrangement with a detection device according to another embodiment of the present invention.

In FIG. 6 there is seen yet another exemplary embodiment according to the present invention, here where the detection device 3 positioned at the closed bottom end of the collection tube 2. Subsequently to having collected a blood sample 12 into the tube 2, the hydrostatic pressure from the liquid sample will cause plasma to pass through the filter 4 which is arranged transversally at the bottom of the tube 2 and further entering the visible detection compartment 6 where assessment of the risk of hemolysis may be done by means of evaluating the hue of the separated plasma.

Figure 7A:
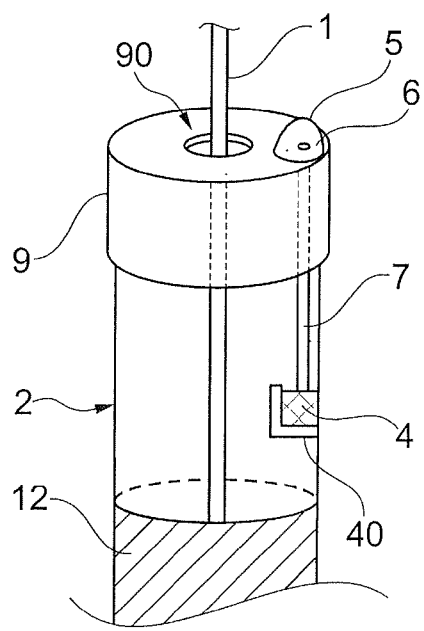
FIGS. 7a-7c illustrate the use of an arrangement according to yet another embodiment of the present invention.
Figure 7B:
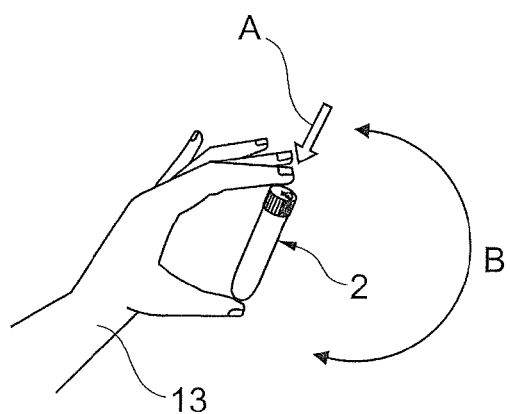
Figure 7C:
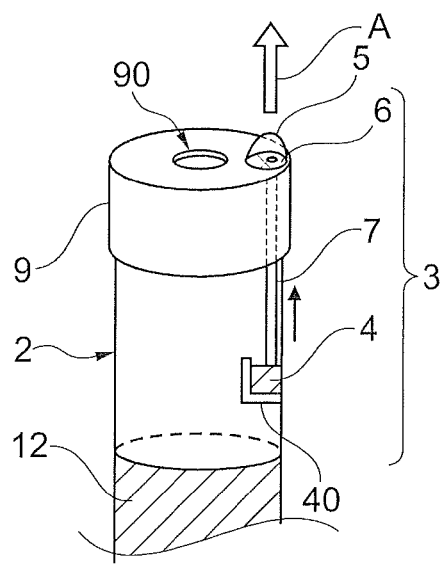

In FIGS. 7a-7c is illustrated a blood sample collection arrangement according to another embodiment, and a corresponding method for performing detection of hemolysis therewith.

In FIG. 7a blood sample 12 has been collected in the tube 2 with needle 1. According to the embodiment in FIG. 7a-c, the detection device 3 comprises a shelf-like portion 40 enclosing a filter 4, which filter is connected to a transfer passage 7 leading to a detection compartment 6 covered by a bellow member 5.

Once the blood sample 12 is collected said needle 1 is removed, see FIG. 7c, and the sample collector 13 will manually press the bellow member 5 as indicated with arrow A, at the same time repeatedly inverting the tube 2, indicated with arrow B. Hereby a small portion of blood will be captured inside the shelf, and as illustrated in FIG. 7c, once the collector 13 releases A the bellow member 5 blood plasma will pass from the shelf 40 and proceed through the channel 7 and enter into the detection compartment 6.

Figure 8:
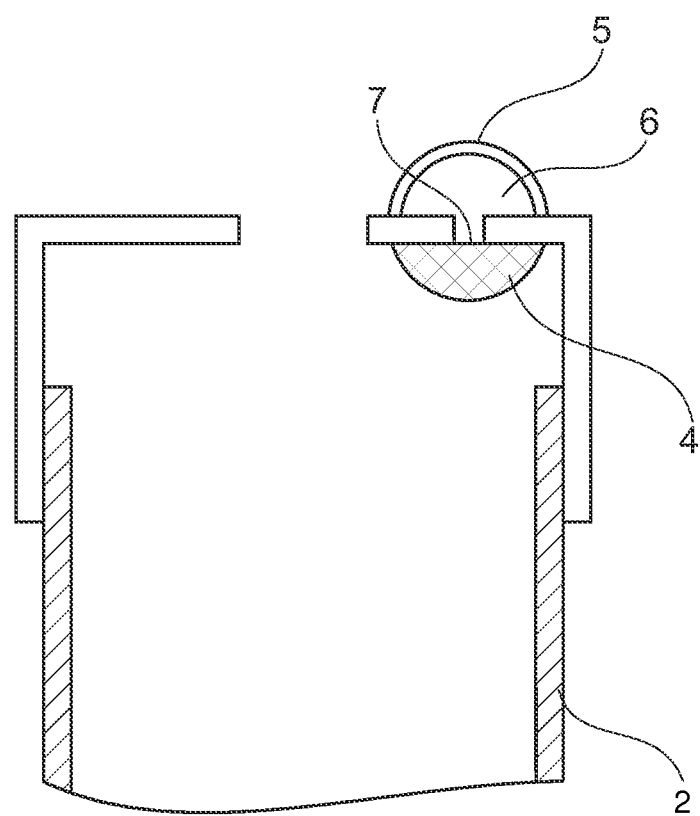
FIG. 8 is a schematic view showing a detail of a blood sample collection arrangement with a detection device according to yet another embodiment of the present invention.

In FIG. 8 is seen yet another embodiment according to the present invention, where a filter 4 is arranged in immediate connection to a detection compartment 6 covered by a bellow member 5. It is to be understood that in an embodiment as disclosed in FIG. 8 the transfer passage 7 corresponds to the separation filter 4 and that the blood plasma will pass from the tube 2 into the detection chamber directly via the filter.

Figure 9A:
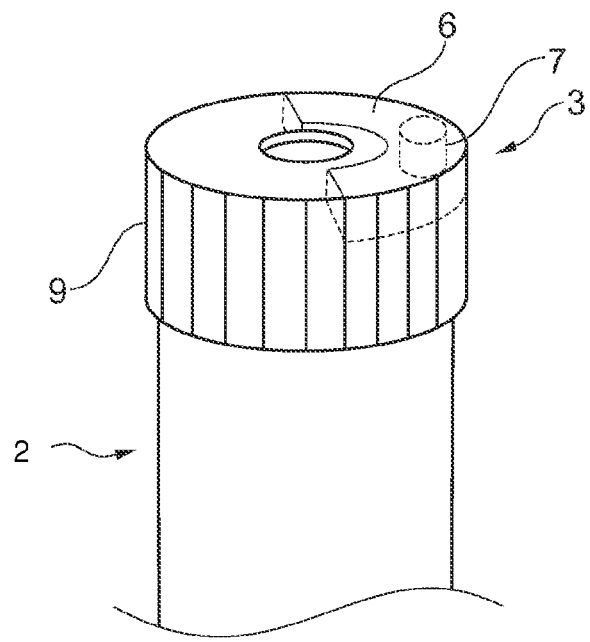
FIGS. 9a-9b show yet another embodiment according to the present invention.
Figure 9B:
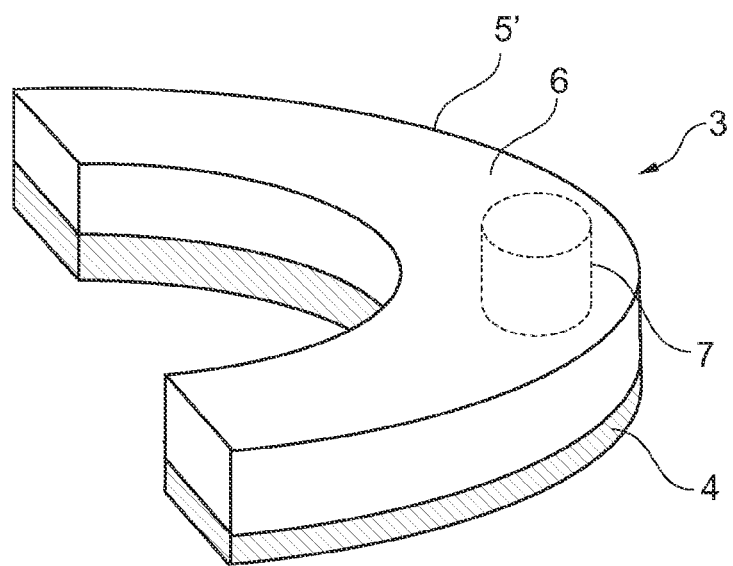

Yet another exemplary embodiment is seen in FIGS. 9a-9b, where FIG. 9a shows an upper portion of a collection tube 2 provided with a detection device 3 visibly positioned at the lid 9 of the blood sample collection arrangement, and FIG. 9b shows an isolated detection device 3 according to the exemplary embodiment. According to this embodiment the detection device 3 comprises a lowermost, transversally extending separation filter 4. A transfer passage, for instance in the form of a channel 7, may be arranged to allow for passage of blood plasma through said filter 4 and into an upper detection compartment 6 shielded by a resilient cover 5'. According to the example shown in FIGS. 9a-9b the resilient cover 5' has the function corresponding to the previously described bellow member 5 and a subpressure is generated in a similar way: by gently pushing against the surface of the cover 5' it will become slightly compressed due to its resilient property. Upon release, the cover 5 will convert to its original shape thereby generating a subpressure which will draw the plasma into the detection compartment 6. Obviously said resilient cover 5' may be combined with/replaced by the previously described bellow member 5. It is further possible that the transfer passage is represented by the filter body 4 meaning blood plasma is arranged to enter into the detection compartment 6 from the chamber of the tube 2 directly via said filter 4, similar to the embodiment shown in FIG. 8. It is further possible that the transfer channel 7 is replaced by some interface or distribution surface, for instance similar to the distribution surface 60 described in connection to FIG. 1b.

In FIGS. 10a-b there is shown a schematic detection device 3 according to one embodiment of the invention, illustrating a principle for generating a subpressure inside a detection compartment 6. In this specific embodiment the "subpressure means" comprises a compressible detection chamber 6 and a spring member 51 which is indirectly connected to said compressible detection compartment 6. The detection compartment shown in FIG. 10a has accordion-like side walls and may hereby be compressed to a substantially flat shape containing a very small volume of air. Adjacent to the detection chamber 6 there is arranged a separation device, e.g. a filter 4, which in its turn is connected to a needle element 1. The needle element is attached to a locking plate 52 which is releasably attached to the side walls of a holding container/housing 16. Said locking plate 52 may be attached to the container 16 e.g. by means of a snap-in mechanism 17 which is easy to unlock. In FIG. 10a shows the detection device 3 (or detection assembly 3) in a state before subpressure has been generated. In this position the locking plate 52 is locked in a position where the spring member 51 is compressed as well as the detection compartment 6. FIG. 10b shows the detection assembly 3 after that the subpressure means has been activated. Generation of subpressure inside the detection compartment 6 is performed as follows. A user pushes a collection tube (not shown) onto the needle element 1 of the device 3 so that the needle penetrates the sealing member of the tube (similar to shown in FIG. 1c). The pushing movement will cause the snap-in mechanism 17 to unlock thereby releasing the locking plate 52 which is pushed in an upward direction C by the biased spring member 51. The locking plate 52 being connected to the needle 1 will hereby cause the needle to also move in the same direction C, and together therewith also the filter 4. As a result the compressed detection compartment 6 will be forced to expand, and the side walls will straighten out, leading to that the interior volume the compartment 6 will also grow larger as the compartment expands and the detection compartment assumes an extended position. This will lead to upcome of a subpressure inside the detection compartment 6 which may be used for transferring blood and separate plasma through the filter 4.

A detection assembly may for instance be delivered to a user in a form corresponding to shown in FIG. 10a, wherein the biasing spring 51 is compressed and the detection assembly 3 ready for use according to the above description.

Yet another possible way of acquiring a subpressure by means of a detection device 3 similar way as seen in FIG. 10a, but instead of creating a subpressure inside the detection compartment 6 (as previously described) creating a subpressure inside the chamber 56 of the housing 16 that withholds the detection compartment 6—i.e. the chamber 56 wherein said spring member 51 and the detection compartment 6 are positioned in FIG. 10a. By means of also providing a valve (e.g. a check valve) connecting the interior of the detection compartment 6 with the chamber, a subpressure generated in the chamber 56 can spread to the detection compartment 6 and initiate whole blood transfer and plasma separation. In such an embodiment a subpressure may be generated by sealing the chamber between the locking plate 52 and the housing 16, and still keeping the locking plate movable 52 while sealed against the inner walls of the housing 16. By means of then moving the locking plate 52 in such a way that the chamber 56 is forced to expand (e.g. upwards in FIG. 10a) while being hermetically sealed a subpressure is created inside the chamber 56, and via a valve member connecting the interior of the detection compartment 6 and the chamber 56 such subpressure will spread to the compartment 6 and draw a plasma sample via the needle 1 and through the filter 4 into the compartment 6. Evidently in such an embodiment the detection compartment 6 does not need to comprises compressible side walls, instead its interior volume may be kept constant throughout a subpressure generating procedure. For this reason it is not required that the needle element 1 is connected to the locking plate 52 since the moving/expansion of the detection compartment 6 is not necessary.

Figure 11B:
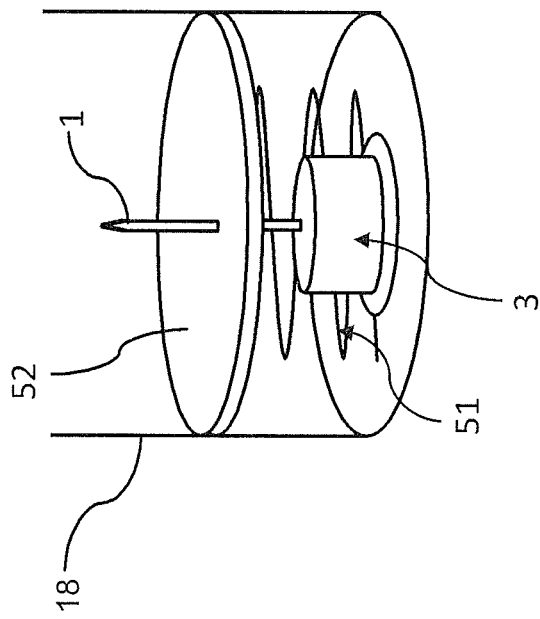
FIGS. 11a-11b show another example of subpressure means and a detection device according to one embodiment of the invention.
Figure 11A:
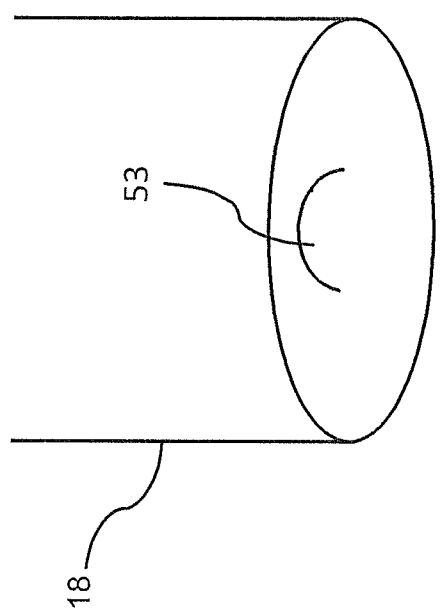

In FIGS. 11a-11b there is shown a schematic detection device 3 according to another embodiment of the invention, illustrating a principle for providing a subpressure inside a detection compartment 6 of a detection device 3 preferably corresponding to a device as described in FIGS. 1a-1e. The example shown in FIG. 11a-11b illustrates a situation where a subpressure is prearranged inside the detection compartment 6, i.e. where a subpressure is already prepared inside the detection compartment 6 when the device is delivered to a user so that a plasma sample will immediately be drawn into the compartment 6 upon use of the device 3, with no need for separate generation of such subpressure. In this specific embodiment the "subpressure means" comprises a protruding structure 53 seen in FIG. 11a and a resilient (compressible) cover membrane 5 covering the detection compartment 6. A protruding structure 53 may for instance be arranged in a holding container 18, as in FIG. 11a, which container 18 is arranged to receive and support a detection device 3. The principle behind the embodiment of FIG. 11a-11b is to keep the resilient cover membrane 5 in a compressed mode, i.e. minimizing the air volume inside the detection compartment 6, until the moment when blood sample is to be drawn into the device 3. At the point when plasma separation is to be initiated the cover membrane 5 is released from the protruding structure 53 so that it may retake its original, neutral shape and will hereby create a subpressure inside the detection compartment 6. This is accomplished in a way which is illustrated in FIGS. 11a-b. The detection device 3 is positioned with its needle member directed upwards on a protruding structure 53 inside a holding container 18, which protrusion 53 preferably is designed to substantially match the depth and width of the detection compartment 6 in such a way that the covering membrane 5 upon being positioned on the protrusion 53 will be compressed so that air is forced to exit out of the detection compartment 6 (for example via a check valve). The device 3 is retained onto the structure 53 and the membrane 5 is kept in a compressed mode until use of the device 3 for detecting hemolysis in a blood sample. One way of retaining the device 3 onto the structure is seen in FIG. 11b. A locking plate 52 is secured onto the side walls of a container 18, said locking plate 52 withholding a detection device 3 onto the protrusion 53 so that the membrane 5 of the device 3 is kept in a compressed state. A biasing spring member 51 is arranged between the bottom of the container 18 and the underside of the locking plate 52. When activating the subpressure means a user pushes a collection tube, with its sealing member facing the needle 1, onto the detection device 3 so that the needle 1 pierces through the sealing member of the tube and contacts the whole blood collected therein. In the same movement the locking plate 52 is unlocked from the side walls of the container 18, for instance by means of unlocking of a conventional snap-in mechanism leading to that the biasing spring member 51 may expand and will force the locking plate 52 to move in an upward direction. Hereby the detection device 3 is lifted from the protrusion 53 and the cover membrane 5 will retain its original uncompressed shape thereby giving rise to a subpressure inside the detection compartment 6 initiating plasma separation process.

It is to be understood that the holding container 18 seen in FIG. 11a may be used as a separate unit for generating a subpressure inside a detection compartment. For instance, a user may press a detection device 3 which is already arranged on a collection tube 2 onto a protruding structure 53 as the one seen in FIG. 11a in order to generate a subpressure.

The skilled person realizes that a large variety of modifications may be performed without the use of inventive skill, departing from the description above, e.g. locating the separation device 4 inside or outside of the tube 2 or varying the placement of the detection compartment 6. Further the detection device 3 may be arranged in such a way integrated with the needle element 1 so that hemolysis can be detected by merely collecting a blood sample with the needle. As is also clear from the description it is understood that the transfer passage may or may not be a transfer channel: for instance the transfer passage may be represented by the body of said separation device 4. Further the subpressure generating device may be a bellow 5 or it may be some other type of subpressure generating device e.g. involving a piston or other suction member.

It is foreseen that separate protection in varying fields of the embodiments described herein may be applied for at a later stage, e.g. by means of divisional.

Many modifications and other embodiments of the inventions set forth herein will come to mind to one skilled in the art to which these inventions pertain having the benefit of the teachings presented in the foregoing descriptions and the associated figures.

Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. Device for visual detection of hemolysis in a whole blood sample, comprising:
  at least one visible detection compartment and a transfer passage connected to said visible detection compartment, said transfer passage being arranged to permit transfer of a volume of plasma from said sample to said detection compartment, wherein:
  said transfer passage is arranged with a separation device for separating plasma from blood cells within said whole blood sample before said plasma reaches said detection compartment,
  said detection compartment and said separation device are arranged within a housing,
  said transfer passage comprises a needle element having a first end portion for penetrating the sealing member of a blood collection tube and a second end portion arranged at a first end of the housing and in connection to said separation device,
  said device is arranged with an air-displacing member able to provide a subpressure inside said detection compartment for generating a force urging said volume of plasma to be transferred from said whole blood sample to said detection compartment through said transfer passage and via said separation device, which air-displacing member is arranged at a second end of the housing,
  said first end of the housing being opposite to said second end of the housing, and
  said housing is configured so that when the device is positioned vertically on a horizontal surface said air-displacing member will be positioned on the side of the device which faces said horizontal surface and the needle element will at the same time point in an upward direction.

2. Device according to claim 1, wherein said air-displacing member is a transparent and resilient membrane covering the detection compartment which resilient membrane is arranged to be compressible, and wherein the detection compartment further comprises a valve, said valve being arranged to allow for air passage out of the detection compartment and prevent air passage into the detection compartment, wherein compression of the resilient membrane covering will lead to exit of air through the valve, and wherein the membrane cover is arranged to strive to retake its original shape after having been compressed.

3. Device according to claim 1, wherein said transfer passage comprises a transfer channel creating a distance between the separation device and the detection compartment.

4. Device according to claim 1, wherein the separation device is a filter having a cross sectional filter area which is at least ten times larger than the cross sectional area of said transfer passage.

5. Device according to claim 1, wherein said at least one detection compartment is arranged with chemical means arranged to react with hemoglobin for direct visual detection of hemolysis.

6. Device according to claim 1, wherein said detection compartment is arranged with compressible side walls and wherein the detection compartment can be shifted between a compressed position and an extended position, wherein the interior volume of the detection chamber in said extended position is larger than the interior volume of the detection chamber in said compressed position, wherein said device comprises a spring member arranged to apply a biasing force urging the detection compartment to assume an extended position.

7. Device according to claim 1, wherein said detection compartment is arranged within a hermetically sealed chamber, and wherein said chamber is connected to the interior of the detection compartment, preferably via a valve, wherein a subpressure can be generated inside the chamber in such a way that said subpressure is spread to the interior of the detection compartment.

8. Device according to claim 1, wherein said detection compartment is arranged within a hermetically sealed chamber, and wherein said chamber is connected to the interior of the detection compartment via a valve, wherein a subpressure can be generated inside the chamber in such a way that said subpressure is spread to the interior of the detection compartment.

9. A holding container for a device according to claim 2, comprising a protruding structure arranged to be brought into contact with said resilient membrane covering so that placing the device into the holding container will result in compression of said membrane and exit of air out of the detection compartment through the valve.

10. Method for detecting hemolysis in a whole blood sample comprising the steps of:
  a. providing a device for visual detection of hemolysis in a whole blood sample, comprising at least one visible detection compartment and a transfer passage connected to said visible detection compartment;
  b. providing a whole blood sample and bringing the device into contact with the sample,
  c. simultaneously with contacting the device with the sample generating a subpressure inside the detection compartment for urging a volume of plasma to be transferred from said sample to said detection compartment through the transfer passage and via a separation device for separating plasma from blood cells within said whole blood sample; and d. inspecting plasma inside the detection compartment in order to detect hemolysis.

\* \* \* \* \*